United States Patent [19]
Cargill et al.

[11] Patent Number: 5,667,933
[45] Date of Patent: Sep. 16, 1997

[54] IMAGE-RECORDING ELEMENT

[75] Inventors: Gary E. Cargill, Millis, Mass.;
Edward C. Taylor, Princeton, N.J.;
Peter Viski, Lexington, Mass.;
Christopher E. R. Orvig, Vancouver, Canada

[73] Assignee: Polaroid Corporation, Cambridge, Mass.

[21] Appl. No.: 753,180

[22] Filed: Nov. 20, 1996

Related U.S. Application Data

[63] Continuation-in-part of Ser. No. 607,680, Feb. 26, 1996, abandoned.
[51] Int. Cl.$^6$ .................. G03C 8/02; G03C 8/40
[52] U.S. Cl. .......... 430/200; 430/203; 430/218; 430/222; 430/617; 430/955
[58] Field of Search .................. 430/203, 222, 430/218, 617, 9.55, 200

[56] References Cited

U.S. PATENT DOCUMENTS

| | | | |
|---|---|---|---|
| 3,260,598 | 7/1966 | Yutzy et al. | 430/206 |
| 4,559,291 | 12/1985 | Neumann et al. | 430/222 |
| 4,740,363 | 4/1988 | Hirai et al. | 430/203 |
| 4,740,445 | 4/1988 | Hirai et la. | 430/203 |
| 4,880,723 | 11/1989 | Hirai et al. | 430/203 |
| 5,415,970 | 5/1995 | Arnost et al. | 430/203 |

*Primary Examiner*—Richard L. Schilling
*Attorney, Agent, or Firm*—Jennifer A. Kispert

[57] ABSTRACT

There are described heat-developable photosensitive image-recording elements which have an alkali-generating system incorporated therein. In the alkali-generating system, a slightly water-soluble metal compound is reacted with a salt of 2-hydroxy-pyridine-N-oxide, or its derivatives, in the presence of a fluid such as water, to form an insoluble precipitate and the alkali required for silver image development during processing. The image-recording materials are useful as image-forming materials in thermographic and photothermographic processes.

33 Claims, No Drawings

IMAGE-RECORDING ELEMENT

CROSS-REFERENCE TO RELATED APPLICATIONS

This application is a continuation-in-part of prior application, Ser. No. 08/607,680 filed Feb. 26, 1996, now abandoned.

BACKGROUND OF THE INVENTION

The present invention relates to a heat-developable photosensitive image-recording element and, more particularly, to an image-recording element which has an alkali-generating system incorporated therein.

In conventional photographic systems, a light-sensitive photographic element containing a photosensitive silver halide emulsion layer is exposed to form a latent image, then the exposed silver halide is developed to a visible silver image by a developer solution. Such a developer solution typically contains an alkaline activator to obtain a pH at which the silver halide can be effectively developed. It is well known in the art that, in general, the developer activity increases as the mount of alkali in the developer is increased, that is, as the pH of the solution is increased above 7.5. A developer solution containing no alkali, produces very little if any silver image development in an exposed photographic element.

The alkaline environment required for development may be provided by any of a number of known techniques. For example, an aqueous alkaline processing composition may be distributed to the image-recording element after exposure of the photosensitive silver halide emulsion such as from a rupturable container as is well known in the diffusion transfer photographic art. Alternatively, the alkali may be generated in situ in the manner described in U.S. Pat. Nos. 3,260,598; 4,740,363; and 4,740,445.

The term "alkali" is generally defined as a material that is generated for the purpose of, or which causes, substantial deprotonation of a component of the thermally processable system such as organic and inorganic salts of hydroxide, e.g., alkali metal hydroxides, ammonium hydroxides, and highly basic organic materials.

It is well known in the art that providing the alkaline environment required for development by incorporating alkaline compounds in photosensitive materials which are then stored for a period of time may result in the discoloration of color images formed and the coloration of white areas due to, among other things, the action of coexisting silver halide, silver complex, developing agents, the hydrolysis of gelatin, and the like. Additional disadvantages exist with respect to using alkalies, i.e., irritation of the skin upon direct contact with the alkali, neutralization of the alkalinity due to absorption of carbon dioxide in air, susceptibility to aerial oxidation and, in general, the lessened stability of developer solutions having increased pH.

As mentioned previously, the alkaline environment required for development may be generated in situ by incorporating an alkali-generating system in the image-recording element as opposed to, for example, being distributed to the image-recording element as an aqueous alkaline processing composition from a rupturable container.

U.S. Pat. No. 3,260,598 discloses a system in which the alkali needed for developing agent activation is generated in the area where development is to take place. The system uses a light-sensitive photographic element that incorporates in the light-sensitive layer or an adjacent layer an alkali-releasing agent comprising a slightly water soluble metal hydroxide, the element being developed with a low alkali developer solution containing an alkali-releasing reagent which reacts with the metal hydroxide to form a substantially less dissociated compound and release the hydroxyl ions needed to activate the development reaction.

U.S. Pat. No. 4,740,363 discloses a process for generating alkali which includes reacting a complexing agent with a slightly water-soluble metal compound in the presence of water.

U.S. Pat. No. 4,740,445 discloses an image forming reaction system including a difficultly soluble metal compound and a compound capable of water-mediated complexing reaction with the metal ion of the difficultly soluble metal compound and having an organic base, by reacting the two compounds in the presence of water to increase the pH of the system.

Heat-developable photosensitive imaging materials are well known in the art, including thermally developable black and white, as well as, color photosensitive materials. Image-recording materials useful in photographic imaging systems including any of the known diffusion transfer color photographic processes such as thermographic and photothermographic typically contain a support carrying a photosensitive silver halide emulsion and a silver halide developing agent.

A visible image is formed in photothermographic image-recording elements by exposing the photosensitive silver halide emulsion to an imagewise pattern of activating light to form a latent image and subsequently applying heat to the element in the presence of the developing agent. The photosensitive silver halide emulsion may serve as the sole source of silver for forming the final image, e.g., the light-sensitive silver may be developed to form a final negative image in reduced (metallic) silver. Alternatively, the photosensitive silver halide emulsion may not be the sole source of silver for forming the final image, e.g., a non light-sensitive source of silver such as a silver salt may be utilized. For example, the exposed photosensitive silver halide emulsion, upon being heated, catalyzes an oxidation-reduction reaction between the non light-sensitive silver salt and the developing agent to form a visible image.

As the state of the art for image-recording elements of this type advances, novel techniques and materials continue to be developed by those skilled in the art in order to attain the performance criteria required of such materials. The present invention relates to a novel heat-developable photosensitive image-recording element and, more particularly, to an image-recording element which has the novel alkali-generating system incorporated therein.

SUMMARY OF THE INVENTION

There is provided according to the invention a heat-developable photosensitive image-recording element which incorporates an alkali-generating system therein. In the alkali-generating system of the present invention, a ligand exchange reaction occurs between a slightly water-soluble metal compound and a salt of 2-hydroxy-pyridine-N-oxide, or its derivatives, in the presence of a fluid, to form an insoluble precipitate and the alkali required for silver image development during processing.

The alkali-generating system incorporated in the image-recording materials of the present invention may be used in any suitable image-recording element including photothermographic and thermographic to form, e.g., a final black and white image in reduced silver or a color image by transferring dyes or dye precursors, e.g., dye developers, to an image-receiving layer as a function of imagewise heating or exposure, in the presence of a fluid, preferably, water. For thermographic applications, the image-recording material generally includes a silver salt oxidizing material which may function as the sole silver ion source or as an additional source when a photosensitive silver halide is present. If the image-recording element is to be used to generate a full color-image, it generally has three different heat-developable light-sensitive layers each releasing a different color dye as a result of thermal development.

Any suitable chemical imaging system may be used in the present invention; however, preferably, the chemical imaging system is a competitive (or parallel) imaging system, e.g., $Ag^+$ catalyzed dye release reactions, dye-developer systems and electron transfer-induced release of dye.

The heat-developable photosensitive diffusion transfer materials of the present invention include those wherein the photosensitive silver halide emulsion layer(s) and the image-receiving layer are initially contained in separate elements which are brought into superposition subsequent or prior to exposure. Alternatively, the photosensitive layer(s) and the image-receiving layer may initially be in a single element wherein the negative and positive components are contained in a heat-developable laminate or otherwise retained together in an integral structure. In either case, after heat development the two elements may be retained together in a single film unit, i.e., an integral negative-positive film unit or they can be peeled apart from one another.

Heat-developable photosensitive image-recording elements according to the invention have been found to provide good silver development and image dye densities in the resulting photographs which also exhibit decreased background areas, i.e., $D_{min}$ values.

These and other objects and advantages which are provided in accordance with the invention will in part be obvious and in part be described hereinafter in conjunction with the detailed description of various preferred embodiments of the invention. The invention accordingly comprises the processes involving the several steps and relation and order of one or more of such steps with respect to each of the others, and the product and compositions possessing the features, properties and relation of elements which are exemplified in the following detailed disclosure, and the scope of the application of which will be indicated in the claims.

DETAILED DESCRIPTION OF THE PREFERRED EMBODIMENTS

The image-recording elements of the present invention have an alkali-generating system incorporated therein which provides the alkaline environment required for effective development of the photosensitive silver halide.

According to the alkali-generating system incorporated in the heat-developable photosensitive image-recording elements of the invention, a ligand is reacted with a slightly water-soluble metal compound in the presence of a fluid such as water to form an insoluble precipitate and the alkali required for effective photosensitive silver halide development:

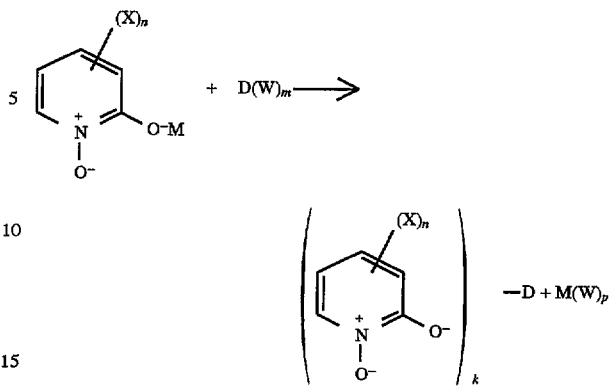

The ligand, i.e., a salt of 2-hydroxy-pyridine-N-oxide, or its derivatives, is represented by formula (I)

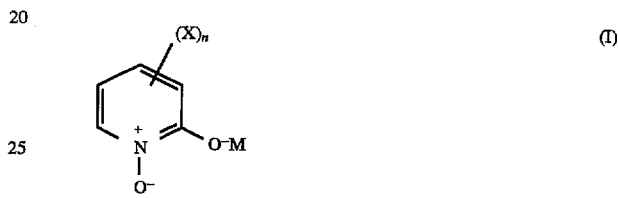

wherein:

X can be a hydrogen atom or a substituent such as, for example, a halogen atom, cyano, nitro, hydroxyl, substituted or unsubstituted alkyl having from 1 to 6 carbon atoms, cycloalkyl such as cyclohexyl, aryl such as benzene, alkenyl such as $CH_2=CH-$, alkynyl such as $CH\equiv C-$, alkoxy such as methoxy, aryl-oxy such as phenoxy, acyl, amino, acylamino, 5- or 6-membered heterocyclic radicals containing O, S or N as heteroatoms, alkylsulfonyl such as $CH_3-SO_2-$, arylsulfonyl, or carbamoyl such as $CH_3-NH-C=O$, n is an integer from 0 to 4; and M is a photographically acceptable cation and can be inorganic such as lithium, potassium, cesium or sodium or organic such as guanidine, cyclic guanidine, amidine, cyclic amidine, tetraalkyl ammonium hydroxide, piperidine, piperazine, ethylenediamine, N,N'-dimethylethylenediamine, acetamidine, diazabicyclononene, diazabicycloudecene, tetramethyl ammonium hydroxide, tetraethyl ammonium hydroxide, aliphatic amine such as trialkyl amine, hydroxylamine, aliphatic polyamine, aromatic amine such as N-alkyl-substituted aromatic amine, N-hydroxyl-alkyl-substituted aromatic amine and bis[p-(dialkylamino)phenyl]methane, heterocyclic amine, heterocyclic amidine, cyclic amidine and compounds of the following structural formulae:

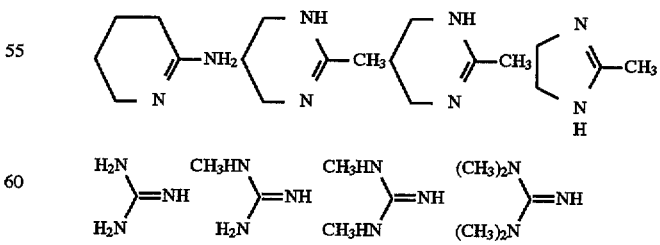

The ligands of the present invention can be prepared using reactions which are known in the art, for example, such as described in DE 3626210 C1; ES 2 008 339; Chem. Abstracts, 89: 120508a, 146419w and 197347k (1978); R.

Adams and W. Reifschneider, *The Reaction of 2-Bromopyridine N-Oxides with Active Methylene Compounds* (1957); F. K. Rafla and M. A. Khan, *Cyclic Hydroxamic Acids. Part I. Synthesis and Reactions of 1,2-Di-hydro-1-hydroxy-4,6-dimethyl-2-oxopyridine-3-carbonitrile,* J.Chem. Soc. (C), page 2044–2048 (1971); R. Adams and S. Miyano, *Condensation Reactions of Picoline 1-Oxides* (1954); and these will be apparent particularly in view of the specific examples provided herein. Illustrative examples of the ligands within the scope of the present invention are represented by the formulae below:

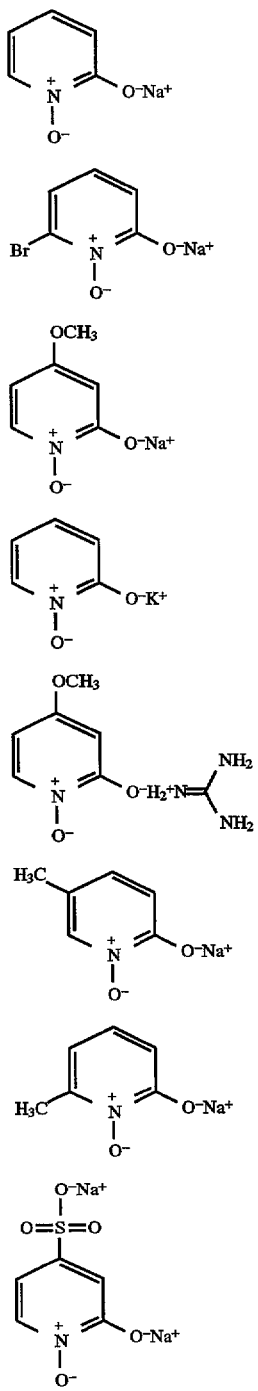
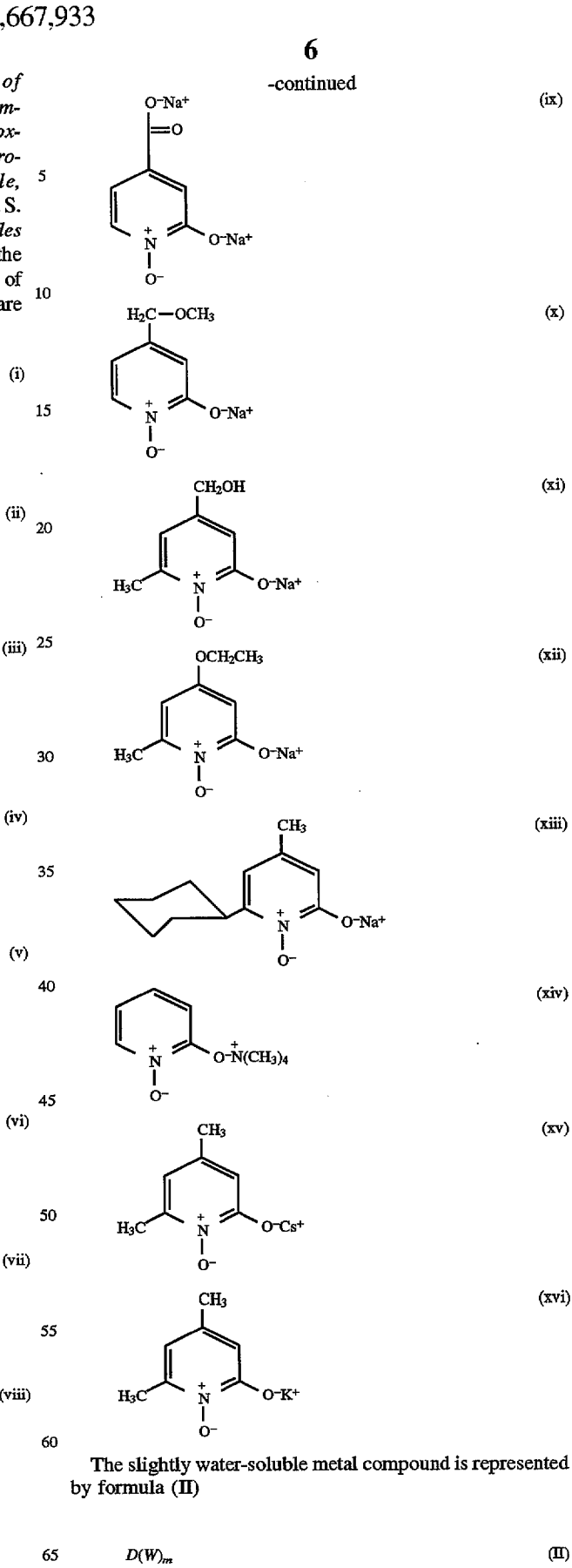

The slightly water-soluble metal compound is represented by formula (II)

$$D(W)_m \qquad\qquad (II)$$

wherein:

D represents a metal other than an alkali metal; typical suitable metals are barium, calcium, cobalt, iron, manganese, nickel, titanium, aluminum and zinc;

W is a photographically acceptable counterion such as, for example, oxide, hydroxide, and carbonate; and m is a positive integer selected so as to establish equilibrium between the valences of D and W.

Illustrative examples of the slightly water-soluble metal compound used in the alkali-generating system of the present invention include zinc oxide and zinc hydroxide.

The insoluble precipitate is represented by formula (III)

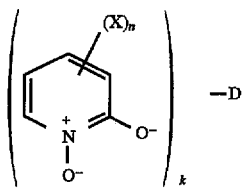

wherein:

X, D and n are as described above; and k is 1, 2 or 3.

The alkali that is generated by the ligand exchange reaction is represented by formula (IV)

$$M(W)_p \qquad (IV)$$

wherein:

M and W are as described above; and p is a positive integer selected so as to establish equilibrium between the valences of M and W.

To summarize, in the present invention a ligand exchange reaction occurs between a slightly water-soluble metal compound, preferably, zinc oxide, and a ligand, preferably, compound (i) or compound (iv), in the presence of a fluid, preferably, water, wherein the photographically acceptable cation of the ligand, coordinates the metal ion from the slightly water-soluble metal compound and, in turn, alkali is generated. The generation of the base increases the pH of the system by generally 2 to 3 pH units, e.g., from pH 9 to pH 11.5, thus providing the alkaline environment required for effective development of the photosensitive silver halide.

The alkali-generating materials incorporated in the image-recording elements of the present invention should be in a form that is stable and non-migratory or non-diffusible and yet available when needed to generate the base. It will be appreciated by those skilled in the art that the mount of each of the alkali-generating materials, i.e., the slightly water-soluble metal compound, the ligand and the fluid, to be used in a particular system will vary with the choice of system. Furthermore, one of skill in the art will be able to choose suitable amounts of these materials from among the ranges disclosed herein so that they will function as desired in a particular system.

For example, generally in the preferred embodiments of the present invention, as will be described in detail further below, the amounts of the slightly water-soluble metal compound and the ligand used vary with the specific compounds selected but generally an amount of from about 800 mg/m$^2$ to about 3000 mg/m$^2$ per layer for the metal compound and from about 6,000 mg/m$^2$ to about 25,000 mg/m$^2$ per layer for the ligand. As stated earlier, the amount of each material to be used in a given system will be determined by testing various amounts selected from within the ranges disclosed herein.

The alkali-generating materials of the present invention may be a layer on a support of a light-sensitive material or any layer(s) belonging to the light-sensitive and/or image-receiving elements. In embodiments wherein more than one layer is present, the alkali-generating materials may be in one layer or all layers. Preferably, the slightly water-soluble metal compound is incorporated in the photosensitive element of the image-recording material, while the ligand is incorporated in the image-receiving element. By way of illustration, in example I herein, three layers of the photosensitive dement of the image-recording element contain the slightly water-soluble metal compound while one layer of the image-receiving element contains the ligand. By coating the slightly water-soluble metal compound near each of the photosensitive emulsions, as opposed to merely coating the slightly water-soluble metal compound once at either end of the photosensitive element, alkali may be independently generated at the three sites thus avoiding the need to wait for the alkali generated in one location to diffuse to each of the photosensitive layers.

In a preferred embodiment such as the recording member illustrated by example I, it is desirable, as indicated above, to distribute the total amount of slightly water-soluble metal compound in three layers of the photosensitive element in order to expedite image formation; however, as mentioned earlier, the faster image formation may not be the result sought from every image-recording element within the scope of the present invention, hence, the amount of the slightly water-soluble metal compound, as well as the other alkali-generating materials, will vary from system to system depending upon, for example, the desired results.

As stated earlier, the ligand exchange reaction of the alkali-generating system requires the presence of a fluid, preferably, water. Water may be available by any suitable means, for example, by supplying water from without the system, or by previously incorporating water-containing capsules or similar means in the system and breaking the capsules by heating or the like to release the water. In addition, a water-releasing compound may be used which releases water by decomposition during heat development, such as described in U.S. Pat. No. 4,550,071.

As mentioned previously, the alkali-generating system incorporated in the image-recording materials of the present invention may be used in any suitable image-recording element such as, for example, thermographic elements using a silver salt oxidizing material as the sole source of silver ion as described in U.S. Pat. Nos. 5,320,929 and 5,415,970, to form, e.g., a final black and white image in reduced silver or a color image by transferring dyes or dye precursors, e.g., dye developers, to an image-receiving layer as a function of imagewise heating or exposure, in the presence of a fluid, preferably, water. Image-recording elements useful in both black and white and color photographic imaging systems are well known in the art and, therefore, extensive discussion of such materials is not necessary.

Any suitable chemical imaging system may be used in the present invention. Illustrative examples of chemical imaging systems useful in the present invention include non-competitive (or sequential) chemical imaging systems and competitive (or parallel) chemical imaging systems. Non-competitive (or sequential) chemical imaging systems are those wherein a chemical species formed in one reaction takes part in a second following reaction. Examples of such sequential chemical imaging systems are coupler-based systems wherein the oxidized developer, which is the product of the development reaction, then reacts to form or release the dye image. A system of this type is described, for example, in U.S. Pat. No. 3,928,312. Additional examples of this type of system and other cleavage reactions caused by the products of development are described by C. C. Van De Sande, *Angew. Chem. Int. Ed. Eng.*, 22, 1983, 191–209.

Preferably, the chemical imaging system incorporated in the heat-developable photosensitive element of the invention is a competitive (or parallel) imaging system. By a "competitive (or parallel) chemical imaging system" is meant an imaging system wherein a single species such as a silver salt or a reducing agent takes part in two or more reactions which occur simultaneously during the imaging process. Hence there are two or more parallel reaction paths existing (or competing) at the same time for the single chemical species. These competing reactions provide an imagewise distribution of the single species which results in image discrimination. A specific example is where a single chemical species takes part in both the development reaction of silver halide or soluble silver ion or soluble silver ion-containing species and in the reaction that controls the formation or transfer of the imaging material such as an image dye-providing material.

Examples of competitive (or parallel) chemical imaging systems wherein the imaging material is an image dye-providing material and the species involved in both reactions are:

(1) $Ag^+$ catalyzed dye release reactions as described in U.S. Pat. Nos. 3,719,488; 3,719,489; 4,060,417; 4,098,783; and 5,569,574, U.K. Patent Application 1243 046 and in copending, commonly-assigned application, Ser. No. 08/754,286 filed on even date herewith which is a continuation-in-part of prior application, Ser. No. 08/607,296 filed Feb. 26, 1996, now abandoned. $Ag^+$ is involved in both the development and dye release reactions occurring simultaneously. $Ag^+$ is involved in the dye release reaction or consumed by the development reaction with exposed silver halide;

(2) $Ag^+$ complexation and immobilization of dyes as described in U.S. Pat. No. 3,443,941. $Ag^+$ is either developed or complexes with dye molecules to yield a negative image. $Ag^+$ complexes with and immobilizes dyes or is consumed by reaction with exposed silver halide;

(3) pH-controlled diffusion of image dyes as described in U.K. Patent Application 860 234 in which mobile dyes are made immobile by alkali consumption. Herein, alkali ($OH^-$) is consumed in both making dyes diffusible and in the development reaction. Hydroxide anion makes dyes soluble and mobile or is consumed by the development reaction with exposed silver halide;

(4) Dye-developer systems as described in U.S. Pat. No. 2,983,606 and coupler-developers as described in Jap. Pat. 80-07 578 and DE 2 334 035 in which mobile dye species or dye forming species either transfer or are immobilized (consumed) by reaction with exposed silver halide;

(5) Systems wherein a nondiffusible image forming compound does not release a dye or dye precursor by itself but rather releases a dye or dye precursor upon reaction with a reducing agent. In this case, a compound which mediates a redox reaction, i.e., an electron donor, is generally used in combination.

(6) Systems wherein diffusible dyes are released by the action of alkali with ballasted compounds and the reduction of the ballasted compounds prevents release. Such systems are described in U.S. Pat. Nos. 4,199,354 and 4,199,355 and German Patents 2,543,902 and 2,645,656; U.S. Pat. No. 4,139,389 describes a cyclization-based cleavage and European Patent Applications 0 004 399 and 0 038 092 and U.K. Patent application 11445 describe quinone methide reduction. In these schemes $Ag^+$ and the ballasted dye releaser compete for developer prior to alkali attack. Developer molecules reduce the dye releaser and form a diffusible dye or are consumed by the development reaction with exposed silver halide;

(7) Electron transfer-induced release of dye as described in DE 3 008 588, U.S. Pat. Nos. 4,343,893; 4,450,223; 4,609,610; and 4,619,884, and EP 0 220 746. In these mechanisms there is competition between the $Ag^+$ and the immobile dye releasers for the electron transfer material, i.e., the developer. ETA molecules react with the dye releaser to form a diffusible dye or are consumed by the development reaction with exposed silver halide. This process is commonly known as "ROSET" process; and (8) Dye-bleaching imaging systems as described in DE 2 907 435, DE 2 907 437, DE 2 907 440, DE 2 907 436 and U.K. 2 043 282. In these systems there is competition for the silver halide developer material by $Ag^+$ and the cleavable, image dye-releasing material.

As mentioned above, the image-recording elements according to the present invention can be used to form black metallic silver images. Briefly, materials of this sort typically include at least one support carrying in at least one layer: (1) a photosensitive silver halide; (2) a silver halide developer and (3) an image-receiving layer including silver nucleating material. These materials may also include a photoinsensitive silver salt which adds to image density as the silver is reduced. Also, the thermographic image-recording materials of the present invention may use a silver salt oxidizing material as the sole source of silver ion.

The photosensitive material is exposed to an imagewise pattern of activating electromagnetic radiation and subsequently developed at elevated temperature in the presence of alkali, provided, for example, as an aqueous alkaline processing composition in a rupturable container or generated in situ, for example, by incorporating an alkali-generating system in the photosensitive material, both as described above, whereby there is formed in the image-receiving layer a black metallic silver image.

As mentioned above, the image-recording elements according to the present invention can also be used to form color images. Briefly, preferred materials of this sort typically include at least one support carrying in at least one layer: (1) a source of silver ions; (2) a photosensitive silver halide which can also function as the silver ion source; (3) a reducing agent; (4) an image dye-providing material, e.g., a dye-providing compound, and (5) an image-receiving layer; however, the image-receiving layer may be on a separate support. These materials may also include a silver salt oxidizer and a reducing agent for the silver salt. In addition, the photosensitive silver halide may be omitted, and the silver salt oxidizing material may function as the sole source of silver ion.

Preferred color photosensitive imaging materials, e.g., image dye-providing materials such as described in U.S. Pat. No. 5,368,979, are comprised of those which are capable of undergoing cleavage in the presence of the imagewise distribution of silver ions and/or soluble silver complex made available in the undeveloped and partially developed areas of the photosensitive emulsion as a function of development to liberate a more mobile and diffusible image dye-providing moiety in an imagewise distribution corresponding to the imagewise distribution of said ions and/or said complex.

Suitable image dye-providing materials of this preferred type include those containing at least one heterocyclic ring having a 1,3-sulfur-nitrogen or a 1,3-sulfur-oxygen moiety and at least one dye radical, which heterocyclic ring is subject to a cleavage reaction in the presence of silver ions and/or a soluble silver complex to release a diffusible dye. Typical suitable image dye-providing materials of this type are disclosed, for example, in U.S. Pat. Nos. 4,098,783;

5,316,887; 5,320,929; and 5,569,574, and in copending, commonly-assigned application, Ser. No. 08/754,286 filed on even date herewith which is a continuation-in-part of prior application Ser. No. 08/607,296 filed Feb. 26, 1996 now abandoned. Preferred image dye-providing materials include the thiazolidine image dye-providing materials described in U.S. Pat. Nos. 4,098,783 and 5,340,689. The image dye-providing materials may be prepared by techniques known to those skilled in the art and by those disclosed in the previously-mentioned U.S. patents and applications.

Preferably, in the present invention, the image dye-providing material is a color-providing compound, disclosed and claimed in copending, commonly-assigned application, Ser. No. 08/754,286 filed on even date herewith which is a continuation-in-part of prior application Ser. No. 08/607,296 filed Feb. 26, 1996, now abandoned capable, of releasing a diffusible complete dye or dye intermediate upon cleavage in the presence of silver ions or a soluble silver complex, having at least two 1,3-sulfur-nitrogen moieties, represented by formula (V)

$$\begin{array}{c} \text{Dye} \\ | \\ \text{SO}_2 \\ | \\ \text{F—N—(CH}_2)_q\text{—N—E} \\ | \\ \text{X} \end{array} \quad (V)$$

wherein:

Dye represents a complete dye or dye intermediate;

q is 2, 3 or 4;

E and F are each independently hydrogen or

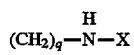

provided that at least one of E and F is

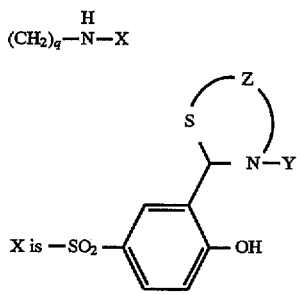

Z represents the carbon atoms necessary to complete an unsubstituted or substituted 5- or 6-membered heterocyclic ring system; and Y represents a photographically acceptable substituent. Typical suitable photographically acceptable substituents include:

(a) linear or branched alkyl ($C_nH_{2n+1}$); preferably having from 1 to 22 carbon atoms;

(b) cycloalkyl such as cyclohexyl;

(c) aryl group such as phenyl, 1-naphthyl, or aralkyl such as

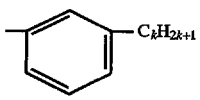

preferably having from 7 to 18 carbon atoms;

(d) heterocyclic group such as 2-pyridyl; and each of (a)–(d) may be substituted with a substituent which can be represented by $R_6$, where $R_6$ can be, for example, halogen such as trifluoromethyl; alkaryl such as

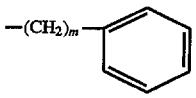

wherein m is 1, 2 or 3, preferably, m is 1; alkenyl having from 1 to 6 carbon atoms such as 2-propenyl; alkoxy having from 1 to 6 carbon atoms such as methoxy or ethoxy; aryloxy such as phenoxy, e.g., 2,4-di-t-amylphenoxy; carbonoxy such as alkylcarbonyloxy, e.g., acetyloxy; alkylsulfonyloxy such as methanesulfonyloxy; amino such as dimethylamino; arylamino such as anilino or p-t-octylanilino; sulfonylamino such as methanesulfonylamino; arylsulfonamino such as p-toluenesulfonyl; cycloalkyl such as cyclohexyl; heterocyclic group such as 2-pyridyl.

As stated previously, Y is preferably alkyl having from 1 to 22 carbon atoms. In a particularly preferred embodiment Y is alkyl having from 1 to 9 carbon atoms such as methyl, ethyl or isopropyl. In another preferred embodiment Y is aralkyl having from 7 to 18 carbon atoms.

In a preferred embodiment, Y is a ballast group, i.e., a group which renders the compound substantially mobile and nondiffusible in the imaging media. When the compounds represented by formula (V) are incorporated in the photographic image-recording elements of the invention, it is necessary that the unsubstituted or substituted 5 - or 6 - membered heterocyclic ring system undergo ring-opening during photographic processing. Thus, since Y is attached to the nitrogen atom of the ring system, any group, e.g., ballast group, which would not interfere with ring-opening is preferred. Groups which would cause such interference are, for example, a sulfonyl group or an acyl group. A preferred ballast group is an alkyl group having at least 10 carbon atoms, and preferably having from 10 to 22 carbon atoms such as $C_{18}H_{37}$ or $C_{22}H_{45}$. Another preferred ballast group is an aralkyl group having at least 12 carbon atoms, and preferably having from 12 to 18 carbon atoms such as

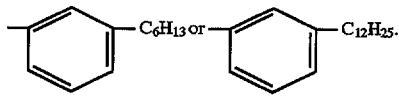

It should also be noted that a ballast group may be also attached to at least one of the carbon atoms represented by Z.

Another way to render the compound of formula (V) of the present invention substantially immobile and nondiffusible in the imaging media is to use additional color-providing moieties as ballast groups, such as disclosed and claimed in, for example, U.S. Pat. No. 5,430,156 wherein the color-providing moieties are connected to each other by multivalent chemical linkages which link the cyclic 1,3-sulfur-nitrogen groups through the nitrogen atom or the carbon atoms of the, e.g., thiazolidine, ring system.

As mentioned above, the image-recording elements of the present invention are useful in photographic imaging systems including any of the known diffusion transfer color photographic processes including thermographic which may use a silver salt oxiding material as the sole source of silver, and photothermographic, and, therefore, extensive discussion of such elements is not necessary.

Briefly, preferred color image-recording elements of the present invention include at least one support carrying in at least one layer: (1) a source of silver ions; (2) a photosensitive silver halide which can also function as the silver ion source; (3) a reducing agent; (4) a compound having at least one cyclic 1,3-sulfur-nitrogen moiety, and (5) an image-receiving layer; however, the image-receiving layer may be on a separate support. Moreover, the image-receiving element for photographic diffusion transfer processing may include not only a support layer, but also, for example, a polymeric acid-reacting layer, a water-permeable and water-absorbing polymeric layer, a water-impermeable polymeric timing layer and a water-permeable and dyeable image-receiving layer as described in U.S. Pat. No. 4,873,171.

Photographic products and processes of the diffusion transfer type are well known and have been described in numerous patents, including, for example, U.S. Pat. Nos. 2,983,606; 3,345,163; 3,362,819; 3,594,164; and 3,594,165. In general, diffusion transfer photographic products and processes involve image-recording materials having a photosensitive system including at least one silver halide layer usually integrated with an image-providing material, e.g., an image dye-providing material. After photoexposure, the photosensitive silver halide is developed, generally by uniformly distributing an aqueous alkaline processing composition from a rupturable container over the photoexposed element, to establish an imagewise distribution of a diffusible image-providing material. The image-providing material is selectively transferred, at least in part, by diffusion to an image-receiving layer or element positioned in a superposed relationship with the developed photosensitive element and capable of mordanting or otherwise fixing the image-providing material. The image-receiving layer retains the transferred image for viewing and in some diffusion transfer products, the image is viewed in the layer after separation from the photosensitive element, while in other products, such separation is not required. A preferred photothermographic diffusion transfer image-recording material will now be described in detail.

The imaging material may be incorporated in the same layer as the photosensitive silver halide emulsion, with or without a silver salt oxidizer, or in a layer on either side of the photosensitive emulsion layer. However, when the imaging materials are image dye-providing materials, e.g., dye-providing compounds, preferably, the materials are incorporated in a layer which is separate from the layer in which the photosensitive silver halide is located and, in those embodiments which include a silver salt oxidizer, also separate from the layer in which the silver salt oxidizer is located.

Also, it is generally preferred that the imaging materials be located such that exposure does not occur through them. For example, when the imaging materials are image dye-providing materials, e.g., dye-providing compounds, if exposure is made through the dye, the dye may absorb some of the light needed to expose the silver halide. Therefore, in certain instances, it may be desirable to separate the imaging material from the photosensitive silver halide layer by a spacer layer. Where the particular image dye-providing material chosen tends to be migratory during storage and/or thermal development of the photosensitive system, it is preferred that the image dye-providing material be in a separate layer and particularly preferably, that it be in the layer farthest from the image-receiving layer.

The amount of image dye-providing material used varies with the type chosen but generally an amount of from about 0.25 to about 2.0 mmol/m$^2$ is used.

The image dye-providing materials may be incorporated into the photographic layer(s) of the heat-developable photosensitive system by any suitable method. For example, the image dye-providing materials can be dissolved in a low boiling and/or high boiling solvent and dispersed in the binder, they can be dispersed in aqueous solutions of suitable polymers, e.g., gelatin, by means of a ball mill, or they can be solvent coated using any organic solvent that will also dissolve the binder, e.g., trifluoroethanol or dimethylsulfoxide.

The photosensitive silver halide emulsion layer(s) and other layers of the heat-developable photosensitive image-recording material may contain various materials as binders. Suitable binders for photosensitive silver halide emulsion layers include water-soluble synthetic, high-molecular weight compounds such as polyvinyl alcohol and polyvinylpyrrolidone and synthetic or naturally-occurring high molecular weight compounds such as gelatin, gelatin derivatives, cellulose derivatives, proteins, starches and gum arabic. A single binder or mixture of binders may be used. Gelatin is the preferred binder for use in each layer. The mount of binder used in each layer is generally from about 0.5 to about 5.0 g/m$^2$, preferably from about 0.5 to about 3.0 g/m$^2$.

The layers of the heat-developable photosensitive system according to the present invention which contain a crosslinkable colloid as a binder, e.g., gelatin, can be hardened by using various organic and inorganic hardeners such as those described in T. H. James, *The Theory of the Photographic Process*, 4th Ed., MacMillan, 1977, pp. 77–87. The hardeners can be used alone or in combination. It is preferred that the image-recording materials according to the present invention contain a hardener in the photosensitive silver halide emulsion layer(s). Any suitable hardener may be used; however, aldehyde hardeners, e.g. succinaldehyde and glyoxal, have been found to be particularly useful when gelatin is employed as the binder. The hardeners are generally used in mounts ranging from 1 to 10% by weight of the total mount of gelatin coated.

The support(s) for the image-recording materials according to the present invention can be transparent or opaque and must necessarily be able to withstand the heat required for processing the image. Any suitable support can be employed such as those described in Research Disclosure No. 17029, issued June 1978. Specific examples of suitable supports include synthetic polymeric films, such as polyester, polyethylene terephthalate, polycarbonate, polyvinyl chloride, polystyrene, polyethylene, polypropylene and polyimide. The above described supports can be made opaque by incorporating pigments therein such as titanium dioxide and calcium carbonate. Other supports include paper supports, such as photographic raw paper, printing paper, baryta paper and resin-coated paper having paper laminated with pigmented thermoplastic resins, fabrics, glass and metals. Preferably, a polyester film is used.

A subcoat may be added to the face of the support which carries the heat-developable photosensitive materials in order to increase adhesion. For example, a polyester base coated with a gelatin subcoat has been found to enhance adhesion of aqueous based layers.

As mentioned above, in the alkali-generating system, a slightly water-soluble metal compound is reacted with a ligand in the presence of a fluid such as water, to form an insoluble precipitate and the alkali required for silver image development during processing. In embodiments of the present invention wherein the thermographic image-recording elements are processed in the absence of water, a thermal solvent may act as the fluid required for alkali generation. The thermal solvent may be incorporated in one or more layers in the photosensitive and/or image-receiving elements.

Thermal solvents which are useful in heat-developable imaging elements and methods are nonhydrolyzable, thermally stable compounds which are solids at ambient temperatures but which melt at or below the temperature used in thermal processing. The thermal solvent acts as a solvent for various components of the heat developable photosensitive material, assists in the acceleration of thermal development and provides the medium for diffusion of various components including silver ions and/or silver complexes, reducing agents and image dye materials.

As stated earlier, water is the preferred fluid for the alkali-generating system of the present invention; however, in its absence, any suitable thermal solvent(s) may act as the fluid for alkali generation. Many suitable thermal solvents for use in photothermographic imaging elements are known in the art such as those described in U.S. Pat. No. 3,667,959. In addition, typical suitable thermal solvents, preferably for use with gelatin, the preferred binder, and some of their properties are described in U.S. Pat. No. 5,368,979.

The photosensitive silver halide used in the present invention may be any photosensitive silver halide employed in the photographic art, such as, silver chloride, iodide, bromide, iodobromide, chlorobromide, etc. and it may be prepared in situ or ex situ by any known method including using a light-sensitive silver halide forming component in the presence of the silver salt oxidizing material so as to form the light-sensitive silver halide in part of the silver salt oxidizer.

The photosensitive silver halide emulsions are typically aqueous silver halide emulsions, and any convenient silver halide precipitation methods may be used. The photosensitive silver halide emulsions may be spectrally sensitized by any suitable spectral sensitization method in order to extend the photographic sensitivity to wavelengths other than those absorbed by the silver halide. Examples of suitable sensitizers include cyanine dyes, merocyanine, styryl dyes, hemicyanine dyes and oxonole dyes. In addition to spectral sensitization, the silver halide emulsion may be chemically sensitized using any suitable chemical sensitization technique. Many chemical sensitization methods are known in the art.

The silver halide emulsion is generally added to each photosensitive layer in an amount calculated to give a coated coverage in the range of 0.5 to 8.0 mmol/m$^2$, preferably 0.5 to 4.0 mmol/m$^2$.

As mentioned previously, the heat-developable photosensitive image-recording element according to the present invention may also include a photoinsensitive silver salt or a silver salt oxidizer. The silver salt oxidizing material utilized in certain embodiments should be relatively light stable and thermally stable under the processing conditions. Accordingly, the silver salt oxidizing material is generally an organic silver salt or silver salt complex as heretofore known in the art. Any organic compound known in the photographic art to be useful for forming the organic silver salt may be employed, see, e.g., those described in U.S. Pat. No. 4,729, 942. See U.S. Pat. No. 4,260,677 for useful silver salt complexes. Examples of suitable silver salt oxidizing materials include silver salts of carboxylic acids, e.g., behenic and stearic acids and silver salts of compounds having an imino group. Preferred silver salts are the organic silver salts having an imino group. The photothermographic and the thermographic color image-recording materials may also include an auxiliary ligand, e.g., methylthiomethyluracil, for silver.

The silver salt oxidizer used in thermographic, i.e., silver salt with or without photosensitive silver halide, and photothermographic, i.e., photosensitive silver halide with or without silver salt oxidizing material, embodiments of the present invention can be prepared in a suitable binder by any known means and then used immediately without being isolated. Alternatively, the silver salt oxidizer may be isolated and then dispersed in a suitable binder. The silver salt oxidizer is generally used in an amount ranging from 0.5 to 12.0 mmol/m$^2$, and preferably from 0.5 to 4.0 mmol/m$^2$.

Any suitable reducing agents may be used in the image-recording elements of the present invention, and these may be selected from among those commonly used in heat-developable photographic materials. Illustrative reducing agents useful in the present invention include inorganic reducing agents such as sodium sulfite and sodium hydrogen sulfite; hydroxylamines; hydrazines; hydrazides; boranamine complexes; hydroquinone and its derivatives, for example, 2-dalorohydroquinone; aminophenol derivatives, e.g., 4-aminophenol and 3,5-dibromophenol; catechol and its derivatives, e.g., 3-methoxycatechol; phenylene-aliamine derivatives, e.g., N,N-diethyl-p-phenylenediamine; 3-pyrazolidone derivatives, e.g., 1-phenyl-3-pyrazolidone, 1,5-phenyl-3-pyrazolidone and 4-hydroxy-methyl-4-methyl-1-phenyl-3-pyrazolidone; 3-pyrazolidinones; hydroxy-tetronic acids; ascorbic acids; and, 4-amino-5-pyrazolones. Preferred reducing agents include 1-phenyl-3-pyrazolidone, commercially available under the tradename Phenidone, 4-hydroxymethyl-4-methyl-1-phenyl-3-pyrazolidone, commercially available under the tradename Dimezone-S, and 4-methyl-phenidone, commercially available under the tradename Graphidone. Reductone developer agents, e.g., aminoreductone, are commonly used in heat-developable photosensitive image-recording elements, for example, as described in U.S. Pat. No. 5,427,905; and, in photothermographic materials, for example, as described in U.S. Pat. Nos. 4,433,037; 4,550,071; and 4,639,407.

The reducing agents which may be used singly or in combination in the present invention are generally employed in mounts ranging from 0.5 to 10.0 mmol/m$^2$, and preferably 1.0 to 8.0 mmol/m$^2$.

Reducing agent precursors which do not have a reducing property by themselves but may express a reducing capacity with the aid of a nucleating reagent or under heat during the step of development may also be employed. Examples of reducing agent precursors which may be employed in the present invention are described in U.S. Pat. Nos. 5,336,761 and 4,500,626.

As stated earlier, the heat-developable photosensitive image-recording material according to the present invention can be used to form monochrome or multicolor images. If the image-recording element is to be used to generate a full color-image, it generally has three different heat-developable light-sensitive layers each releasing a different color dye as a result of thermal development.

Where multicolor images are desired, one or more layers containing a scavenger for silver ion and/or soluble silver complex may be employed between the photosensitive emulsion layers to enhance color separation. By virtue of the silver scavenger layer(s) positioned between the emulsion layers, the migration of the imagewise distribution of soluble silver ions or soluble silver complex formed during processing of each emulsion layer is confined to the dye-providing material associated with each emulsion layer and prevented from diffusing into the dye-providing material associated with the other emulsion layer(s). Accordingly, silver scavengers which may be employed in the present invention include those described in U.S. Pat. No. 4,060,417. Likewise, scavengers for oxidized developing agents which may be employed in the present invention include those described in U.S. Pat. No. 3,482,971.

As mentioned previously, the heat-developable photosensitive diffusion transfer materials of the present invention include those wherein the photosensitive silver halide emulsion layer(s) and the image-receiving layer are initially contained in separate elements which are brought into superposition subsequent or prior to exposure. After development the two elements may be retained together in a single film unit, i.e., an integral negative-positive film unit or they can be peeled apart from one another. If the two elements are peeled apart, a separate strip coat layer may be present on the image-receiving layer as a means of facilitating separation of the image-receiving layer from a photosensitive layer. The strip coat can be prepared from a variety of hydrophilic colloid materials. Hydrophilic colloids for a strip coat include gum arabic, carboxymethyl cellulose, hydroxyethyl cellulose, carboxymethyl hydroxyethyl cellulose, cellulose acetatehydrogen phthalate, polyvinyl alcohol, polyvinyl pyrrolidone, methyl cellulose, ethyl cellulose, cellulose nitrate, sodium alginate, pectin, polymethacrylic acid, polymerized salts or alkyl, aryl and alkyl sulfonic acids (e.g., DAXAD, W. R. Grace Co.), polyoxyethylene polyoxypropylene block copolymers (e.g., Pluronic F-127, BASF Wyandotte Corp.) or the like.

Alternatively, rather than being in separate elements, the photosensitive layer(s) and the image-receiving layer may initially be in a single element wherein the negative and positive components are contained in a heat-developable photosensitive laminate or otherwise retained together in an integral structure. After heat-development, the two layers may be retained together as a single element or they can be peeled apart from one another. Where the photosensitive silver halide emulsion layer(s) and the image-receiving layer are retained together as an integral negative-positive film unit, a masking layer, e.g., titanium dioxide, may be necessary to conceal the untransferred dye-providing material and other products from photothermographic development from the final image.

Where the image-recording elements of the invention comprise separate elements which are brought together prior, or subsequent, to exposure, it is preferred that the image dye-providing material be located in a layer which underlies the silver halide emulsion layer which in turn, underlies the organic silver salt layer, if the silver salt is included. In this embodiment, it is preferred to expose the photosensitive layer through the outermost layer, so that the exposure is not made through the image dye-providing material, prior to superimposing the two separate elements in order to carry out the remaining steps of the photothermographic processing. Similarly, in a preferred embodiment wherein all the layers of a heat-developable photosensitive image-recording material are carried by one support, it is preferred to arrange the image-receiving layer adjacent the support and underlying, in succession, the image dye-providing material layer, the silver halide emulsion layer and the organic silver salt layer, if the silver salt is included. Exposure is preferably made through the outermost layer; however, other possibilities exist as described below.

The image-receiving layer is generally superposed on the photosensitive negative after exposure and the two are then heated simultaneously to develop the image and cause the dye to transfer. Alternatively, the negative may be exposed and then processed with heat, followed by superposing the image-receiving sheet on the exposed and developed photosensitive material and applying heat and pressure to transfer the dye. The image-receiving layer is then generally peeled apart from the negative.

As mentioned above, film products comprising sheets that are separated after processing are described as "peel-apart" films. In integral films, the sheets, together with a rupturable container containing an aqueous alkaline processing composition such as described in U.S. Pat. No. 3,719,489, or an alkali-generating system such as described herein, are retained as sealed film units, providing images that are ready for viewing without separation of the two sheets. One integral color print film structure comprises a multilayer negative sheet and a positive sheet preassembled with a pod, or an alkali-generating system, for example, of the present invention, and sealed together at the edges, as described in U.S. Pat. No. 3,415,644. In these film units, exposure and viewing of the image take place through the same surface. An alternative integral film configuration provides both emulsion and receiving layers as coatings on the same support, in combination with the spreader sheet. This film unit is exposed through one surface and the image is viewed through the opposite surface, as described in U.S. Pat. Nos. 3,594,165 and 3,689,262; Belgian Patent 757,960; and Hanson, W. T., Jr. 1976, "A Fundamentally New Imaging Technology for Instant Photography," *Photogr. Sci. Eng.*, 20, 155–160. Embodiments of the present invention include the alternative film configurations described above. Regardless of the film configuration utilized, as mentioned previously, it is preferred to incorporate the slightly water-soluble metal compound in the photosensitive element of the image-recording material, while incorporating the ligand in the image-receiving layer of the image-recording material to avoid any unwanted alkali-generation.

The photosensitive material of the present invention may be exposed by any of the methods used in the photographic art, e.g., a tungsten lamp, a mercury vapor lamp, a halogen lamp, fluorescent light, a xenon flash lamp or a light emitting diode including those which emit infrared radiation.

As mentioned above, the photosensitive material of the present invention is heat-developed after imagewise exposure. This is generally accomplished by heating the material at a temperature in the range of 80° to 160° C., preferably in the range of 80° to 120° C., for a period of from 1 to 720 seconds, preferably 1.5 to 180 seconds. Any method of heating that can be employed in heat-developable photosensitive systems may be applied to the heat-developable photographic material of the present invention. Thus, for example, heating may be accomplished by using hot air, a hot plate, an iron, heated rollers or a hot drum. Heat may be used alone or heat may be applied simultaneously with pressure, if necessary, to create good thermal contact between the photosensitive and image-receiving materials. Pressure can be applied simultaneously with the heat required for thermal development by using heated rollers or heated plates. Alternatively, heat and, if required, pressure can be applied subsequent to thermal development in order to transfer the released dye.

Any image-receiving layer capable of receiving an image dye-forming compound made available as a result of photographic development may be utilized in the color image-recording materials of the invention. Typical image-receiving layers which can be used are prepared by coating a support material with a suitable polymer for receiving the dye. Suitable polymers to be coated on the image-receiving support to receive dye include polyvinyl chloride, poly(methyl methacrylate), polyesters, and polycarbonates. Alternatively, certain polymers may be used as both the support and the dye-receiving material.

Various polymeric materials have been utilized as mordants in photographic products and processes including those of the diffusion transfer type. The mordants used herein may be selected from a variety of mordants although polymeric mordants are preferred. Thus, polymeric mordants suited to application in diffusion transfer products and processes for the formation of photographic images in dye are described, for example, in U.S. Pat. Nos. 3,148,061; 3,758,445; 3,770,439; 3,898,088; 4,080,346; 4,308,335; 4,322,489; 4,563,411; 4,749,067; and 5,395,731. The mordant layer for use with the image-recording element of the invention which has an alkali-generating system incorporated therein preferably includes poly-4-vinylpyridine (P4VP), polyvinylalcohol (PVA), crosslinkers and a surfactant.

Additionally, the heat-developable photosensitive image-recording material of the present invention optionally may include other materials known in the art for use in photo-thermographic image-recording elements. These include, but are not limited to, antifoggants such as benzotriazole, 6-nitrobenzimidazole and those described in U.S. Pat. No. 4,743,533, antistatic materials, coating aids, e.g. surfactants such as preferred Triton X-100, activators and the like. Moreover, when the chemical imaging system incorporated in the image-recording material of the invention is a Ag$^+$ catalyzed dye release reaction, other photographically useful groups besides dyes such as antifoggants, development restrainers, dye intermediates, e.g., dye developers, or silver halide solvents, i.e., silver halide complexing agents which form water-soluble silver complexes with the residual silver halide such as those described in U.S. Pat. No. 4,713,313, may be released from, for example, thiazolidines, oxathiolanes, and the like. Furthermore; the image-recording materials of the present invention also include non-imagewise release of, as well as the above-described imagewise release of, e.g., antifoggants, silver halide solvents and the like.

In addition, U.S. Pat. No. 4,743,533 describes a photographic system which utilizes compounds capable of releasing a photographically useful material by a base-catalyzed elimination when contacted with an aqueous alkaline processing composition. Likewise, embodiments of the image-recording materials disclosed and claimed herein include compound(s) which provide controlled release of, e.g., photographically useful group(s), by a base-catalyzed elimination when contacted by the alkali generated from within the materials.

It is known in the art to utilize development restrainers and development restrainer precursors in photographic applications. A predetermined level of development usually will take place before the development restrainers or development restrainer precursors function to inhibit or control further development. The blocked development restrainers are designed to provide a controlled release of the development restrainer during the development process. Such blocked development restrainers are disclosed, for example, in U.S. Pat. Nos. 3,260,597 and 3,265,498 which disclose hydrolyzable blocked restrainers; U.S. Pat. No. 3,698,898 which discloses the use of quinone- or naphthoquinonemethide precursors which release a photographic reagent such as 1-phenyl-5-mercaptotetrazole in the presence of alkali; U.S. Pat. No. 3,938,996 which discloses the use of a carbocyclic blocking group which includes an oxime group (e.g. —C=N—OH); U.S. Pat. No. 4,009,029 which discloses a class of cyanoethyl-containing blocked development restrainers; and German Offenlegungsschrift No. 2,427,813 which discloses various blocked development restrainers. In addition, U.S. Pat. No. 4,946,964 discloses and claims compounds capable of providing controlled release of development restrainers during the development process. Furthermore, as mentioned earlier, the developer itself may be blocked, i.e., reducing agent precursors which do not have a reducing property by themselves but may express a reducing capacity with the aid of a nucleating reagent or under heat during the step of development.

Development activators may also be used such as those described in U.S. Pat. Nos. 2,162,714; 3,173,786; 3,301,678; 3,669,670; 3,839,041; 3,844,788; 3,877,940; 3,893,859; 4,012,260; 4,060,420; 4,677,206; and, in Belgian Patent No. 768,071.

Also, the photosensitive elements optionally may contain additional layers commonly used in the art, such as spacer layers, a layer of an antihalation dye, and/or a layer of a filter dye arranged between differentially color-sensitive emulsion layers and/or a protective layer(s). The protective layer(s) may contain a variety of additives commonly employed in the photographic art. Suitable additives include matting agents, colloidal silica, slip agents, toning agents, organofluoro compounds, UV absorbers, accelerators, antioxidants, etc.

The invention will now be described further in detail with respect to specific preferred embodiments by way of an example, it being understood that this is intended to be illustrative only, and the invention is not limited to the materials, procedures, amounts, etc. recited therein. All parts and percentages recited are by weight unless otherwise stated.

In the following example, the light-sensitive layers used a pure silver bromide 0.92 μm mono-dispersed emulsion prepared by standard techniques known in the art. Sensitization was performed using a spectral dye first technique known in the art. The blue-sensitive emulsion did not use a blue spectral sensitizing dye. The green emulsion used a green spectral sensitizing dye. The red emulsion used a red spectral sensitizing dye. The red and green emulsions were also chemically-sensitized using gold and sulfur.

The dye-providing material and the reducing agents used in the example were added to the coating compositions as dispersions. The various dispersions were prepared by the specific procedures described below or by analogous procedures but using different reagents as noted. In addition, images have been obtained using a broad range of emulsion with respect to grain size, iodide levels, sensitization and morphology. The other components of the layers, e.g., succinaldehyde, when added were added to the coating compositions as aqueous solutions.

(1) Zinc Oxide Dispersion 5 g of zinc oxide powder (particle size of 0.1 microns), 0.3 g of 25% aqueous Daxad-30 and 14.7 g of water were allowed to grind for 24 hours using ⅛" mullite beads in an attritor. The dispersion was diluted with water during the isolation of the beads from the zinc oxide to a concentration of approximately 20%.

(2) Dispersion of Color-Providing Compounds 5.0 g of dye (yellow, magenta or cyan) and 5.0 g of 10% aqueous Airvol-205 (PVA) were added to 10.0 g of water. This mixture was then allowed to grind for 48 h (yellow or magenta) or for 24 hours (cyan) in an attritor using ⅛" mullite beads. The dispersion was diluted with water during isolation of the dye from the beads to a concentration of approximately 20%.

(3) Silver Ligand Dispersion 5.0 g of Compound (A), i.e., 6-butylthiomethyluracil, 1.0 g of 20% triton X-100, 5.8 g of 6.5% aqueous Tamol-731 (adjusted to pH 7) and 8.2 g of water were allowed to grind for 24 hours using ⅛" mullite beads in an attritor. The dispersion was diluted with water during the isolation of the beads from the ligand to a concentration of approximately 20%.

(4) Reducing Agent Dispersion 5.0 g of Graphidone B, i.e., 4-methyl-phenidone, 2.5 g of 10% aqueous Alkanol XC, 0.1 g of ascorbyl palmitate and 12.4 g water were allowed to grind for 24 hours using ⅛" mullite beads in an attritor. The dispersion was diluted with water during the isolation of the beads from the reducing agent to a concentration of approximately 20%.

(5) Silver Scavenger Dispersion 5 g of Compound D, i.e., scavenger, 2.5 g of 10% aqueous PVA, 1.25 g of 20% aqueous Triton X-100 and 11.25 g of water were first slurried in a meyers mill until a uniform mixture was achieved. The slurry was ground in a Dyno-Mill using 0.8 mm glass beads. After the grinding, the dispersion was homogenized in order to break up aggregates.

(6) Yellow Filter Dye 4.0 g of 7.5% aqueous Tamol-731 was added to a wet cake (5.0 g dry, Compound G, i.e., benzidine yellow 14) and homogenized until a fine suspension was obtained.

(7) Releasable Antifoggant 5.0 g of Compound B, i.e., releasable antifoggant, 3.85 g of 6.5% aqueous Tamol-731 (adjusted to pH 7) and 11.15 g of water were allowed to grind for 24 hours using ⅛" mullite beads in an attritor. The dispersion was diluted with water during the isolation of the beads from the releasable antifoggant to a concentration of approximately 20%.

EXAMPLE I

The following compounds were used in this example:

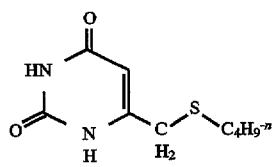

(A)

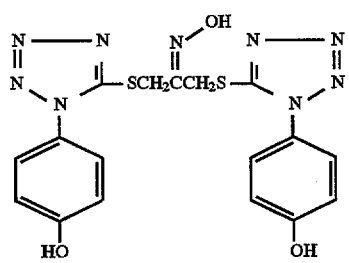

(B)

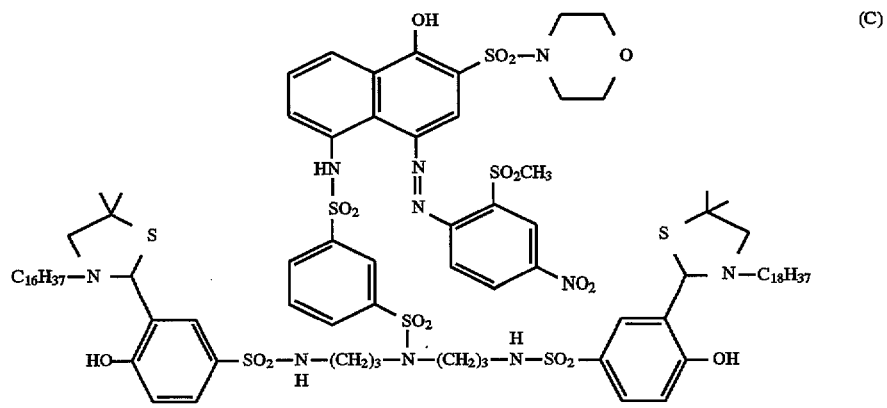

(C)

-continued

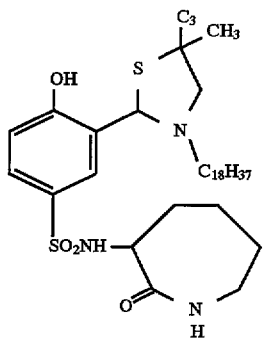
(D)

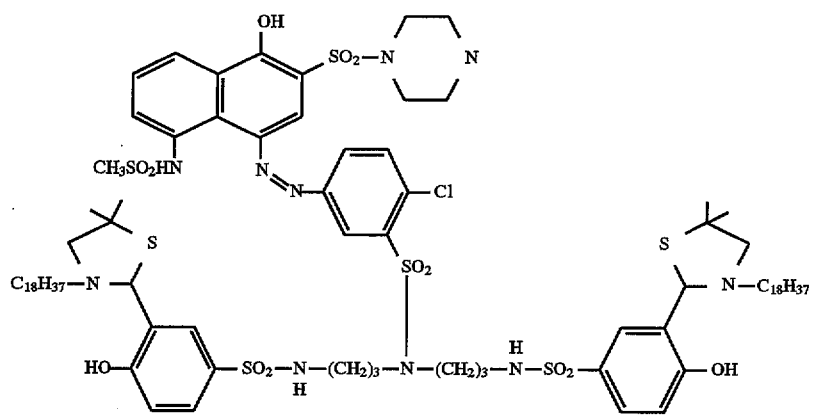
(E)

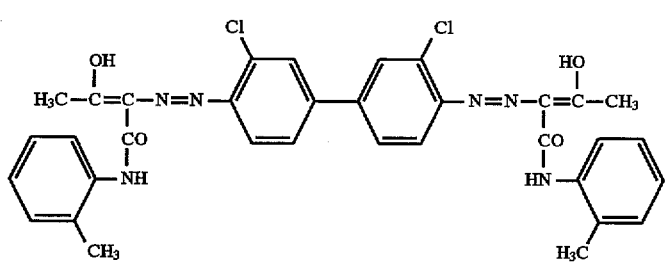
(F)

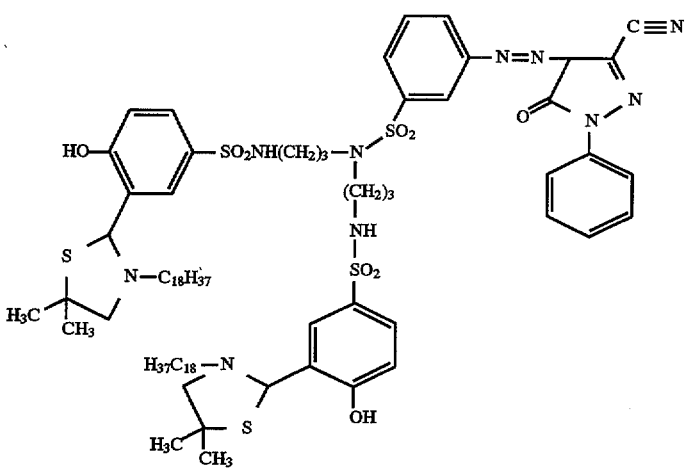
(G)

A heat-developable photosensitive image-recording element was prepared using zinc oxide, a ligand, i.e., Compound (i), and dye-providing compounds according to formula (IV), wherein the photosensitive material comprised a clear polyester film base (carrier SCS) having coated thereon in succession the following layers:

Layer 1

| | |
|---|---|
| Compound A (6-Butylthiomethyluracil) | 430 mg/m$^2$ |
| Compound B | 172 mg/m$^2$ |
| Gelatin | 517 mg/m$^2$ |

| | |
|---|---|
| Graphidone B (4-methyl-phenidone) | 611 mg/m² |
| Compound C (cyan dye-providing compound) | 517 mg/m² |
| Layer 2 | |
| Polyacrylamide | 108 mg/m² |
| Succinaldehyde | 55 mg/m² |
| Layer 3 | |
| Gelatin | 151 mg/m² |
| Emulsion (red-sensitive) | 344 mg/m² |
| Layer 4 | |
| Zinc oxide | 1398.8 mg/m² |
| Gelatin | 538 mg/m² |
| Compound D | 3228 mg/m² |
| Layer 5 | |
| Compound A | 430 mg/m² |
| Compound B | 172 mg/m² |
| Gelatin | 635 mg/m² |
| Graphidone B | 611 mg/m² |
| Compound E (magenta dye-providing compound) | 473 mg/m² |
| Layer 6 | |
| Polyacrylamide | 106 mg/m² |
| Succinaldehyde | 65 mg/m² |
| Layer 7 | |
| Gelatin | 151 mg/m² |
| Emulsion (green-sensitive) | 344 mg/m² |
| Layer 8 | |
| Zinc oxide | 1398.8 mg/m² |
| Gelatin | 538 mg/m² |
| Compound D | 1614 mg/m² |
| Layer 9 | |
| Compound A | 430 mg/m² |
| Compound F | 430 mg/m² |
| Compound B | 172 mg/m² |
| Graphidone B | 611 mg/m² |
| Gelatin | 807 mg/m² |
| Compound G (yellow dye-providing compound) | 1033 mg/m² |
| Layer 10 | |
| Polyacrylamide | 106 mg/m² |
| Succinaldehyde | 65 mg/m² |
| Layer 11 | |
| Gelatin | 151 mg/m² |
| Emulsion (blue-sensitive) | 344 mg/m² |
| Layer 12 | |
| Zinc oxide | 1398.8 mg/m² |
| Gelatin | 538 mg/m² |
| Layer 13 | |
| Gelatin top coat | 200 mg/m² |

The receiver materials of the element comprised the following layers coated in succession on a white-pigmented polyethylene-coated paper base:

| | |
|---|---|
| Layer 1 | |
| P4VP | 4500 mg/m² |
| PVA (Airvol 165) | 900 mg/m² |
| Diepoxy | 37 mg/m² |
| 4010 Acrite 100 (copolymer, formaldehyde and acrolein) | 54 mg/m² |
| Layer 2 | |
| Gum Arabic (TIC Gums) | 220 mg/m² |
| Layer 3 | |
| Gelatin | 2,000 mg/m² |
| Compound (i) | 12,200 mg/m² |
| Gelatin hardener | 340 mg/m² |

Layer 1, i.e., the mordant or "D" coat layer, was coated at a pH of 4.0 adjusted using acetic acid and included Triton X-100 (Union Carbide) as the surfactant at 0.038% based on the total volume of coating solution. Layer 2, i.e., the strip coat, was coated at a pH of 12.0 adjusted using ammonium hydroxide and included Triton X-100 as the surfactant at 0.1% based on the total volume of coating solution. Layer 3, i.e., the chelating layer, was coated at a pH of 8.5 adjusted using potassium hydroxide and included Zonyl FSN (DuPont) as the surfactant at 0.25% based on the total volume of coating solution.

The assembly was processed by dipping the exposed negative in 42° C. deionized water for 5 seconds. Next, the photosensitive element and the image-receiving sheet were laminated using a zero gap rubber roller resulting in the superimposition of the sheet on the wet photosensitive element for 8 seconds. Then, the whole was immediately placed into a waffle iron and heated for 30 seconds at 90° C. Finally, the whole was removed from the waffle iron and peeled apart.

The maximum reflection density ($D_{max}$) and the minimum reflection density ($D_{min}$) of the resulting image were measured using a reflection densitometer (MacBeth, model RD 514):

| | $D_{max}$ | $D_{min}$ |
|---|---|---|
| Red | 1.84 | 0.12 |
| Green | 1.84 | 0.14 |
| Blue | 1.59 | 0.17 |

As will be apparent, example I shows a preferred image-recording element wherein the slightly water-soluble metal compound is located in the photosensitive element while the ligand is located in the image-receiving element. In other embodiments, the slightly water-soluble metal compound is incorporated in the image-receiving element while the ligand is incorporated in the photosensitive element. In yet other embodiments, both the slightly water-soluble metal compound and the ligand are incorporated within the photosensitive element or the image-receiving element. As mentioned above though, the preferred embodiment, with respect to the location of the slightly water-soluble metal compound and the ligand, is as illustrated by example I.

Since certain changes may be made in the above subject matter without departing from the spirit and scope of the invention herein involved, it is intended that all matter contained in the above description and the accompanying example be interpreted as illustrative and not in any limiting sense.

What is claimed is:

1. A heat-developable image-recording element comprising:

a first support and an optional second support and carried by said first support or confined between said first and said second supports;

a layer including a source of silver ions;

an image-receiving layer; and an alkali-generating system comprising a ligand, represented by the following formula

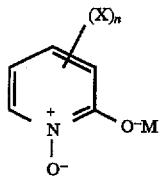

wherein:

X is a hydrogen atom or a substituent selected from the group consisting of a halogen atom, cyano, nitro, hydroxyl, substituted or unsubstituted alkyl having from 1 to 6 carbon atoms, cycloalkyl, aryl, alkenyl, alkynyl, alkoxy, aryl-oxy, acylamino, acyl, amino, heterocyclic radical, alkylsulfonyl, arylsulfonyl, and carbamoyl;

M is a photographically acceptable cation;

n is an integer from 0 to 4; and a slightly water-soluble metal compound represented by the formula $D(W)_m$ wherein D represents a metal other than an alkali metal, W is a photographically acceptable counterion, and m is a positive integer selected so as to establish equilibrium between the valences of D and W.

2. A heat-developable image-recording element as defined in claim 1 wherein said source of silver ions is a photosensitive silver halide.

3. A heat-developable image-recording element as defined in claim 2 which further includes a reducing agent and wherein said image-receiving layer comprises silver precipitating nuclei.

4. A heat-developable image-recording element as defined in claim 2 further including an image dye-providing material in association with said photosensitive silver halide.

5. A heat-developable image-recording element as defined in claim 4 wherein said image dye-providing material comprises a cyan dye, a magenta dye and a yellow dye carried in separate layers on said support.

6. A heat-developable image-recording element as defined in claim 4 wherein said image dye-providing material undergoes a cleavage reaction in the presence of silver ions and/or a soluble silver complex to liberate a color-providing moiety.

7. A heat-developable image-recording element as defined in claim 6 wherein said image dye-providing material is a color-providing compound having the formula

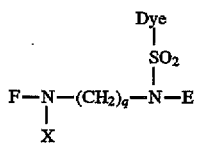

wherein:

Dye represents a complete dye or dye intermediate;

q is 2, 3 or 4;

E and F are each independently hydrogen or

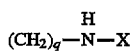

provided that at least one of E and F is

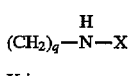

X is

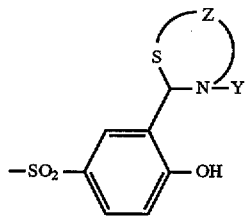

Z represents the carbon atoms necessary to complete a 5- or 6-membered heterocyclic ring system; and Y is a photographically acceptable substituent.

8. A heat-developable image-recording element as defined in claim 7 wherein Z represents the atoms necessary to complete a thiazolidine moiety and Y represents an alkyl group having from 1 to 22 carbon atoms or an aralkyl group having from 7 to 18 carbon atoms.

9. A heat-developable image-recording element as defined in claim 1 wherein said slightly water-soluble metal compound is zinc oxide and said ligand is selected from the group consisting of

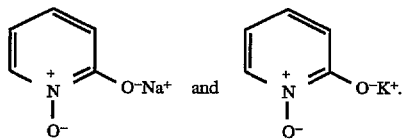

10. A heat-developable image-recording element as defined in claim 1 wherein said source of silver ions is a silver salt oxidizing material.

11. A method of thermal imaging comprising imagewise heating a heat-developable image-recording element as defined in claim 10 in the presence of a fluid whereby photographic development takes place and an image is formed in said image-receiving layer.

12. A method of thermal imaging as defined in claim 11 wherein said fluid is water.

13. A method of thermal imaging as defined in claim 12 wherein said slightly water-soluble metal compound is zinc oxide and said ligand is selected from the group consisting of

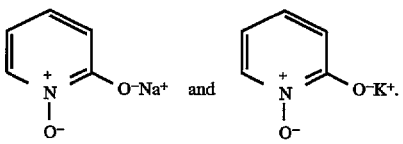

14. A method of thermal imaging as defined in claim 10 wherein said heat-developable image-recording element is initially provided as a photosensitive element and a second element having an image receiving layer, said photosensitive element and said second element in superposed or superposable relationship, and following development, said photosensitive element and said second element are separated from one another.

15. A method of thermal imaging as defined in claim 11 wherein said slightly water-soluble metal compound is contained in at least one layer carried by said first support and said ligand is contained in at least one layer carried by said second support.

16. A heat-developable image-recording element for use in a diffusion transfer color process comprising:

a first support and an optional second support and carried by said first support or confined between said first and said second supports;

a layer including a photosensitive silver halide;

a reducing agent;

an alkali-generating system comprising a ligand represented by the formula

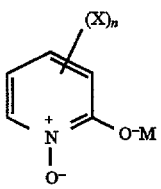

wherein:

X is a hydrogen atom or a substituent selected from the group consisting of a halogen atom, cyano, nitro, hydroxyl, substituted or unsubstituted alkyl having from 1 to 6 carbon atoms, cycloalkyl, aryl, alkenyl, alkynyl, alkoxy, aryl-oxy, acylamino, acyl, amino, heterocyclic radical, alkylsulfonyl, arylsulfonyl, and carbamoyl;

M is a photographically acceptable cation;

n is an integer from 0 to 4;

a slightly water-soluble metal compound represented by the formula $D(W)_m$ wherein D represents a metal other than an alkali metal, W is a photographically acceptable counterion, and m is a positive integer selected so as to establish equilibrium between the valences of D and W;

an image dye-providing material; and an image-receiving layer.

17. A heat-developable image-recording element as defined in claim 16 wherein said image dye-providing material is a color-providing compound.

18. A heat-developable image-recording element as defined in claim 17 wherein said color-providing compound undergoes a cleavage reaction in the presence of silver ions and/or a soluble silver complex to liberate a color-providing moiety.

19. A heat-developable image-recording element as defined in claim 18 wherein said color-providing compound is represented by the formula

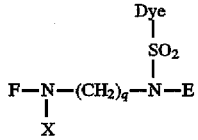

wherein:

Dye represents a complete dye or dye intermediate;

q is 2, 3 or 4;

E and F are each independently hydrogen or

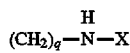

provided that at least one of E and F is

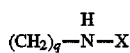

X is

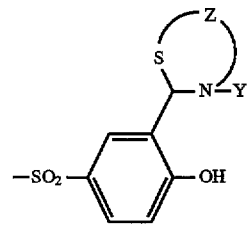

Z represents the carbon atoms necessary to complete a 5- or 6-membered heterocyclic ring system; and Y represents a photographically acceptable substituent.

20. A heat-developable image-recording element as defined in claim 19 wherein Z represents the atoms necessary to complete a thiazolidine moiety and Y represents an alkyl group having from 1 to 22 carbon atoms or an aralkyl group having from 7 to 18 carbon atoms.

21. A heat-developable image-recording element for use in a diffusion transfer color process as defined in claim 16 wherein said slightly water-soluble metal compound is zinc oxide and said ligand is selected from the group consisting of

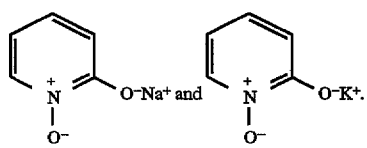

22. A method of thermal imaging comprising imagewise exposing a heat-developable image-recording element for use in a diffusion transfer process as defined in claim 16 and heating said exposed image-recording element in the presence of a fluid whereby photographic development takes place and an image is formed in said image-receiving layer.

23. A method of thermal imaging as defined in claim 22 wherein said fluid is water.

24. A method of thermal imaging as defined in claim 23 wherein said slightly water-soluble metal compound is zinc oxide and said ligand is selected from the group consisting of

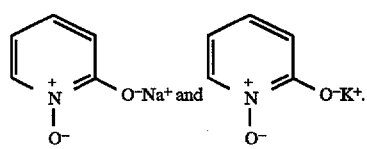

25. A method of thermal imaging as defined in claim 22 wherein said heat-developable image-recording element is initially provided as a photosensitive element and a second element having an image receiving layer, said photosensitive element and said second element in superposed or superposable relationship, and following development, said photosensitive element and said second element are separated from one another.

26. A method of thermal imaging as defined in claim 25 wherein said slightly water-soluble metal compound is contained in at least one layer of said photosensitive element and said ligand is contained in at least one layer of said second element.

27. A heat-developable image-recording element for use in a diffusion transfer black and white process comprising:

a first support and an optional second support and carried by said first support or confined between said first and said second supports;

a layer including a photosensitive silver halide;

a reducing agent;

an alkali-generating system comprising a ligand represented by the formula

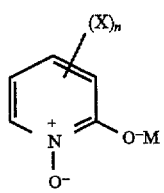

wherein:

X is a hydrogen atom or a substituent selected from the group consisting of a halogen atom, cyano, vitro, hydroxyl, substituted or unsubstituted alkyl having from 1 to 6 carbon atoms, cycloalkyl, aryl, alkenyl, alkynyl, alkoxy, aryl-oxy, acylamino, acyl, amino, heterocyclic radical, alkylsulfonyl, arylsulfonyl, and carbamoyl;

M is a photographically acceptable cation;

n is an integer from 0 to 4;

a slightly water-soluble metal compound represented by the formula $D(W)_m$ wherein D represents a metal other than an alkali metal, W is a photographically acceptable counterion, and m is a positive integer selected so as to establish equilibrium between the valences of D and W; and an image-receiving layer containing silver precipitating nuclei.

28. A heat-developable image-recording element for use in a diffusion transfer black and white process as defined in claim 27 wherein said slightly water-soluble metal compound is zinc oxide and said ligand is selected from the group consisting of

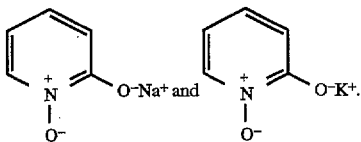

29. A method of thermal imaging comprising imagewise exposing a heat-developable image-recording element for use in a diffusion transfer black and white process as defined in claim 27 and heating said exposed image-recording element in the presence of a fluid whereby photographic development takes place and an image is formed in said image-receiving layer.

30. A method of thermal imaging as defined in claim 29 wherein said fluid is water.

31. A method of thermal imaging as defined in claim 30 wherein said slightly water-soluble metal compound is zinc oxide and said ligand is selected from the group consisting of

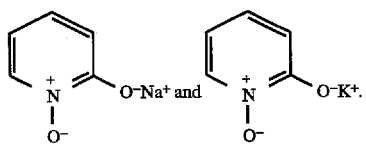

32. A method of thermal imaging as defined in claim 29 wherein said heat-developable image-recording element is initially provided as a photosensitive element and a second element having an image receiving layer, said photosensitive element and said second element in superposed or superposable relationship, and following development, said photosensitive element and said second element are separated from one another.

33. A method of thermal imaging as defined in claim 32 wherein said slightly water-soluble metal compound is contained in at least one layer of said photosensitive element and said ligand is contained in at least one layer of said second element.

* * * * *